United States Patent [19]
Machlowitz et al.

[11] 4,431,633
[45] Feb. 14, 1984

[54] INFLUENZA VACCINE

[75] Inventors: Roy A. Machlowitz, Glenside; Alan C. Herman, Lansdale, both of Pa.

[73] Assignee: Merck & Co., Inc., Rahway, N.J.

[21] Appl. No.: 372,410

[22] Filed: Apr. 27, 1982

[51] Int. Cl.$^3$ .......................................... A61K 39/145
[52] U.S. Cl. ..................................... 424/89; 435/235; 435/238; 435/239
[58] Field of Search .................. 424/89; 435/238, 235, 435/239

[56] References Cited

U.S. PATENT DOCUMENTS 3,031,378  4/1962  Ishidate et al. ....................... 424/89

OTHER PUBLICATIONS

A. R. Neurath et al., Archivfür diegesamte Virusforschung, vol. 28, pp. 421-423 (1969).

Primary Examiner—Thomas G. Wiseman
Assistant Examiner—Frederick W. Pepper
Attorney, Agent, or Firm—Donald J. Perrella; Hesna J. Pfeiffer

[57] ABSTRACT

Influenza virus is extracted with a mixture of ether and ethanol, the aqueous and organic phases are separated and residual ether removed from the virus suspension under reduced pressure. The resulting product is useful as an influenza vaccine.

5 Claims, No Drawings

INFLUENZA VACCINE

BACKGROUND OF THE INVENTION

Attempts have been made to detoxify influenza vaccines by disrupting the influenza virus with detergents, organic solvents or a combination of both. These attempts, however, were not entirely successful because of loss of immunogenic potency.

OBJECTS OF THE INVENTION

It is an object of the present invention to provide an improved method for detoxifying influenza virus without lowering immunogenic potency and, more particularly, to detoxify influenza virus for use in a vaccine by treating the virus with a combination of ether and ethanol. These and other objects of the present invention will be apparent from the following description.

SUMMARY OF THE INVENTION

Influenza virus is extracted with a mixture of ether and ethanol, the aqueous and organic phases are separated and residual ether removed from the virus suspension under reduced pressure. The resulting product is useful as an influenza vaccine.

DETAILED DESCRIPTION OF THE INVENTION

The present invention relates to the detoxification of influenza virus, and, more particularly, to a method for detoxifying influenza virus without lowering its immunogenic potency.

It has now been found that influenza virus may be detoxified without lowering immunogenic potency by treatment with a combination of ether and ethanol.

According to the present invention, influenza virus is delipidated by treatment with a mixture comprising from about 0.5 to about 5, preferably about 1, volumes of diethyl ether plus from about 0.02 to about 0.1 volume of ethanol per volume of aqueous influenza virus-containing fluid.

According to the present invention live influenza virus is concentrated by sedimentation from the egg allantoic fluid in which it was grown and dialyzed against phosphate buffered saline. To the dialyzed concentrate there is added from about 2% to about 10% ethanol. This solution is then mixed with diethyl ether, preferably at a temperature of from about 5° to about 25° C. The mixture separates into two layers, an ether layer and an aqueous layer. The ether layer is discarded and the aqueous layer is stripped of ether by any suitable means, for example by passing an inert gas such as nitrogen through the aqueous layer or by the use of a rotary evaporator under vacuum for a period of from about 1 to about 6 hours, typically for about 2 hours. The resulting influenza virus is inactivated but retains its immunogenic efficacy.

The following example illustrates the present invention without, however, limiting the same thereto. All temperatures are expressed in degrees Celsius.

EXAMPLE 1

Type A/Victoria influenza virus was grown in the allantoic fluid of embryonated eggs, harvested and concentrated by density gradient centrifugation. The sedimentation band containing the influenza virus was isolated and approximately 200 ml of the A/Victoria type were added to each of two 750 ml fluted flasks. Each flask contained a 5 cm stirring bar. 200 Ml of diethyl ether containing 2% ethanol, pre-chilled to 5° were than added to one flask, and 200 ml of diethyl ether containing 10% ethanol, pre-chilled to 5° were then added to the other flask. The resulting mixtures were stirred for 10 minutes and then each was transferred to a 500 ml separatory funnel. After 5 minutes to allow for phase separation, each aqueous phase was removed and transferred to a 500 ml round bottom flask and rotary evaporated in the cold using a 15° water bath and a water aspirator. The evaporation was continued until the ether concentration was below 100 μg/ml (approximately 120 minutes). The virus preparations were then transferred to suitable vessels and stored at 5°.

Hemagglutinating activity was determined by rocket immunoelectrophoresis. Influenza A/Victoria antiserum was used at a concentration of 5 μl/ml in the gel.

Protein was determined by the method of Lowry using bovine serum albumin as a protein standard. Ethanol and ether were determined by gas chromatography.

Lipid material in the organic phase was measured by the phospho-vanillin method.

EXAMPLE 2

Type B/Hong Kong influenza virus was treated similarly to the A/Victoria in Example 1 except that for determining hemagglutinating activity, influenza type B/Hong Kong anti-serum was prepared in guinea pigs from Bromelain purified hemagglutinin and was used at a concentration of 3 μl/ml per gel.

The following results were obtained:

| Ethanol-Ether Extraction - Summary | | A/Vic | | B/HK | |
|---|---|---|---|---|---|
| | | 2% | 10% | 2% | 10% |
| μg HA ml | Start | 510 | 510 | 350 | 350 |
| | End | 520 | 490 | 240 | 200 |
| | % Yield | 100 | 96 | 68 | 58 |
| μg/protein ml | Start | 1900 | 1900 | 1400 | 1400 |
| | End | 2200 | 1600 | 1200 | 1100 |
| | % Yield | 100 | 84 | 85 | 82 |
| Residual ethanol (μg/ml) | Vaccine | 14 | 55 | 14 | 64 |
| Residual Ether (μg/ml) | Vaccine | 4 | 17 | 4 | 5 |
| Lipid Removed (μg/ml) | Vaccine | 13 | 17 | 6 | 11 |

EXAMPLE 3

The following tables show in vivo activity of influenza vaccine treated according to the process of the present invention.

TABLE 1

Geometric Mean Titers of Mice 21 Days Postinjection with A/Victoria Influenza Virus Vaccine

| | HA Units/0.25 ml | | | | |
|---|---|---|---|---|---|
| Vaccine | 20 | 6.25 | 2 | 0.625 | 0.2 |
| Whole Non-Inactivated | 103.7 | 113.1 | 61.7 | 43.6 | 19.5 |
| Whole HCHO Inactivated | 67.3 | 36.7 | 25.9 | 8.7 | 2.8 |
| Whole Non-Inactivated Treated with 2% Alcohol-Ether | 146.7 | 80.0 | 47.6 | 13.8 | 8.7 |
| Whole Non-Inactivated Treated with 10% | 87.2 | 67.3 | 47.6 | 21.8 | 5.0 |

TABLE 1-continued

Geometric Mean Titers of Mice 21 Days Postinjection with A/Victoria Influenza Virus Vaccine

| | HA Units/0.25 ml | | | | |
|---|---|---|---|---|---|
| Vaccine | 20 | 6.25 | 2 | 0.625 | 0.2 |
| Alcohol-Ether | | | | | |

TABLE 2

Number of Positive Responses of Mice 21 Days Postinjection with A/Victoria Influenza Virus Vaccine

| | HA Units/0.25 ml | | | | |
|---|---|---|---|---|---|
| Vaccine | 20 | 6.25 | 2 | 0.625 | 0.2 |
| Whole Non-Inactivated | 8/8 | 8/8 | 8/8 | 8/8 | 7/8 |
| Whole HCHO Inactivated | 8/8 | 8/8 | 8/8 | 6/8 | 3/8 |
| Whole Non-Inactivated Treated with 2% Alcohol-Ether | 8/8 | 8/8 | 8/8 | 7/8 | 6/8 |
| Whole Non-Inactivated Treated with 10% Alcohol-Ether | 8/8 | 8/8 | 8/8 | 8/8 | 5/8 |

TABLE 3

Relative Potencies of A/Victoria Influenza Virus Vaccines

| | Reference Vaccine | | | |
|---|---|---|---|---|
| Vaccine | A | B | C | D |
| Whole Non-Inactivated (A) | — | 8.07 | 2.17 | 2.86 |
| Whole HCHO Inactivated (B) | 0.12 | — | 0.27 | 0.35 |
| Whole Non-Inactivated Treated with 2% Alcohol-Ether (C) | 0.46 | 3.71 | — | 1.31 |
| Whole Non-Inactivated Treated with 10% Alcohol-Ether (D) | 0.35 | 2.83 | 0.76 | — |

TABLE 4

Geometric Mean Titers of Mice 21 Days Postinjection with B/Hong Kong Influenza Virus Vaccine

| | HA Units/0.25 ml | | | | |
|---|---|---|---|---|---|
| Vaccine | 20 | 6.25 | 2 | 0.625 | 0.2 |
| Whole Non-Inactivated B/HK | 190 | 147 | 113 | 57 | 34 |
| Whole HCHO Inactivated B/HK | 87 | 48 | 34 | 28 | 22 |
| B/HK treated with 2% Alcohol-Ether | 103 | 113 | 48 | 13 | 8 |
| B/HK treated with 10% Alcohol-Ether | 73 | 36 | 13 | 25 | 13 |

What is claimed is:

1. A method for preparing an immunogenic influenza vaccine which comprises extracting aqueous live influenza virus with a mixture containing from about 98% to about 90% ether and from about 2% to about 10% ethanol.

2. A method according to claim 1 wherein the extraction takes place at a temperature of from about 5° to about 25° C.

3. A method according to claim 1 wherein the ether layer is discarded and the inactivated yet immunogenic influenza virus is recovered from the aqueous phase.

4. A method for preparing an immunogenic influenza vaccine which comprises extracting live influenza virus with a mixture comprising from about 0.5 to about 5 volumes of diethyl ether plus from about 0.02 to about 0.1 volume of ethanol per volume of live aqueous influenza virus.

5. A method according to claim 4 wherein the mixture comprises about 1 volume of diethyl ether plus from about 0.02 to about 0.1 volume of ethanol per volume of live aqueous influenza virus.

* * * * *